United States Patent [19]

Ootsubo

[11] Patent Number: 4,846,682
[45] Date of Patent: Jul. 11, 1989

[54] METHOD OF FABRICATING ARTIFICIAL DENTURES

[76] Inventor: Tatsuo Ootsubo, 1-14, Akebono-machi, Oomuta-shi, Fukuoka-ken, Japan

[21] Appl. No.: 95,239

[22] Filed: Sep. 11, 1987

[30] Foreign Application Priority Data

Sep. 22, 1986 [JP] Japan .............................. 61-224107

[51] Int. Cl.[4] ...................... A61C 13/00; A61C 13/10; B28B 1/00
[52] U.S. Cl. .................................... 433/167; 249/54; 264/18; 425/2
[58] Field of Search .................. 264/16–19; 433/214, 213, 60, 167, 212.1, 223, 222.1, 207, 206; 249/54; 425/2

[56] References Cited

U.S. PATENT DOCUMENTS

| | | | |
|---|---|---|---|
| 2,316,631 | 4/1943 | Schwartz | 264/18 |
| 2,442,847 | 6/1948 | Galley | 264/17 |
| 2,472,492 | 6/1949 | Saffer | 156/293 |
| 2,491,147 | 12/1949 | Zahn | 156/293 |
| 2,896,265 | 7/1959 | Chambers | 264/17 |
| 2,899,712 | 8/1959 | Smith | 264/18 |
| 3,217,067 | 11/1965 | Tencate | 264/18 |
| 4,115,488 | 9/1978 | Colpitts | 264/17 |
| 4,690,787 | 9/1987 | Fasnacht | 264/16 |

Primary Examiner—Jan H. Silbaugh
Assistant Examiner—Karen D. Kutach
Attorney, Agent, or Firm—Jones, Tullar & Cooper

[57] ABSTRACT

A method of fabricating "adjustment-free" artificial dentures and a jig therefor. A precise jaw model is formed by pouring soft plaster into the concave surface of a precise provisional denture formed by any conventional dental procedure. A plaster block is formed having a recess conforming to the actual shape of the provisional denture. The recess is filled with a synthetic resin compound and then the precise jaw model is moved into the recess to form a plenum defined by the concave surface in the recess and the convex surface of the precise jaw model. During polymerization, any excess synthetic resin compound spilling over from the plenum can escape into a relatively wide clearance between the precise jaw model and the plaster block thus enabling the plenum to retain its original shape. The use of the precise jaw model eliminates the prior art problems associated with a narrow gap inherently formed between the contiguous surfaces of the upper and lower plaster blocks of the conventional flask, into which the curing synthetic resin compound penetrates to disturb the dimensional relationship of the plenum.

8 Claims, 3 Drawing Sheets

METHOD OF FABRICATING ARTIFICIAL DENTURES

BACKGROUND OF THE INVENTION

This invention relates to prosthodontics and, more particularly, to a method of fabricating "adjustment-free" dentures using a jig especially adapted for use in carrying out such method.

Artificial dentures must be accurately reproduced and accurately conform to mouth conditions existing prior to any extractions. However, it has long been the feeling that a certain number of "adjustment visits" are always necessary when making a set of dentures for a patient. During such visits, the doctor sees to it that:

(1) the patient can wear the dentures satisfactorily for eating and talking;

(2) he has no "sore spots" to be relieved;

(3) the upper and lower teeth will fit together to provide the natural bite and follow the relative motion established by masticating motion of his jaw structure; and (4) the act of swallowing will not be hampered by the dentures.

Adjustments are usually made a few times before the final delivery of a completely finished set of dentures. It would be desirable to eliminate such annoying and sometimes painful "adjustment visits" almost entirely.

Various dental procedures for fabricating artificial dentures are currently available, a typical one of which includes the following steps:

1. A set of wax bite blocks is made as negative impressions of the upper and lower gum arches, in order to form a set of wax models for denture bases.

2. Artificial teeth are then attached to the wax models.

3. The next operating step is to form a lower plaster block using a metallic container conventionally called "flask" and consisting of upper and lower sections and top and bottom closure members. For this operation, a mixture of plaster material and water, or soft plaster, is poured into the flask's lower section with the bottom closure member and, the wax model is then submerged in the mixture but not entirely, leaving only small foot portions thereof above the level of the mixture. The soft plaster solidifies, providing the lower plaster block.

4. The wax model provided in the lower plaster block is then coated with a separating material to facilitate separating the lower plaster block from an upper plaster block to be described later. The upper section of the flask is then attached to the lower section and is filled with soft plaster to the level that submerges the wax model entirely. The upper section of the flask is then firmly closed by the upper closure member using a suitable fastening means, and the entire flask is left for a certain period of time until the soft plaster solidifies.

5. After the soft plaster has solidified, the flask is placed in a hot water bath to melt the wax model in the plaster assembly. The flask is then taken out from the hot water bath and opened. It will be observed that the wax model no longer retains its original shape. With the wax washed away, the artificial teeth extend into a cavity formed in the plaster assembly that exactly conforms to the actual shape of the wax model.

6. A pasty synthetic resin compound which is prepared by pouring a monomer into a mixing jar, slowly adding a synthetic resin powder, and stirring continuously until it will thicken due to its own reaction, is poured into the cavity while still soft enough to run. The flask is then closed and placed into a hot water bath to cause the synthetic resin compound to cure or harden due to polymerization induced by the heat from the hot water.

7. After the flask is taken out from the hot water bath, the plaster assembly is carefully broken apart to provide a denture comprising the artificial teeth planted on the denture base formed of the synthetic resin compound.

FIG. 1a illustrates the conventional dental procedure just described for making artificial dentures. The lower plaster block 20 is shown to have the cavity which is formed by submerging the wax model (not shown) in the soft plaster which solidifies to provide the lower plaster block 20. Since the wax model carries artificial teeth 22 (only one of which is shown for brevity of illustration), the teeth have their tips extending into the plaster block. As described above, after the lower plaster block 20 is formed, the concave surface 24 of the lower plaster block is coated with a separating material so as to make it easier to open the flask for the subsequent operation of washing away the wax model.

The upper plaster block 26 is formed by pouring soft plaster into the upper section of the flask to the depth that entirely submerges the wax model. After solidifying of the soft plaster, the flask is opened to expose the wax model within the cavity defined by the recess or concave portion of the lower plaster block 20 and the convex portion of the upper plaster block 26. Thereafter, the wax model which has lost its original shape due to the heat from the hot water bath is washed away, as described above.

It will be noted that the practice of this conventional procedure using the metallic two-section flask inherently entails the formation of an interface between the upper and lower plaster blocks. This interface will tend to cause a serious problem that in the subsequent polymerization step the curing synthetic resin compound will penetrate into a narrow gap 29 between the contiguous surfaces of the upper and lower plaster blocks despite the use of a special press which firmly holds the flask throughout the curing and cooling cycle. When this occurs, the denture does not fit the prescription precisely, causing adjustment problems. Also, the press which is used to apply the high pressure to the flask's upper and lower sections to avoid displacement of these sections is quite costly.

Accordingly, it is the principal object of this invention to provide an improved method of fabricating comfortable and well-fitted dentures with a view to overcoming the deficiencies of the prior art.

It is another object of this invention to provide an improved method of fabricating artificial dentures without use of the conventional two-section flask which, when assembled, inherently creates a narrow gap between the contiguous surfaces of the upper and lower plaster blocks, into which the curing synthetic resin compound penetrates thereby causing adjustment problems.

It is still another object of this invention to provide an improved method of fabricating artificial dentures, which enables the use of a regular prosthetic press in place of an expensive heavy duty press conventionally used by the prior art method.

It is a further object of this invention to provide a jig especially adapted for use in carrying out the method of this invention.

SUMMARY OF THE INVENTION

The objects stated above and other related objects in this invention are accomplished by carrying out a method of fabricating an artificial denture, comprising: making a precise provisional denture comprising a denture base and a plurality of artificial teeth thereon, the denture base having a concave surface conforming to the actual shape of an edentulous ridge in a patient's mouth; making a precise jaw model from the concave surface of the denture base; forming a block of plaster or other hardenable material having a recess therein that conforms to the actual shape of the precise provisional denture, the artificial teeth having their tips extending into the block and their roots extending into the recess; filling a synthetic resin compound into the recess of the block; forcing the precise jaw model to move into the recess of the block to mold the synthetic resin compound therein into an artificial denture; subjecting the synthetic resin compound to polymerization reaction to cause the compound to cure and solidly fill a plenum defined by the convex surface of the precise jaw model and the concave surface in the recess of the block; and, breaking the block apart upon solidification of the synthetic resin compound to provide a finished denture; wherein any synthetic resin compound spilling over from the plenum during polymerization escapes into a wide clearance between the precise jaw model and the block, thereby resulting in the finished denture conforming to the exact shape of the precise provisional denture.

This invention also resides in a jig for use in fabricating an artificial denture, comprising: a base; at least two posts affixed to and extending upwardly from the base; a top plate adapted to be mounted to the posts in parallel to the base; means for removably mounting the top plate to the posts; means for removably mounting a jaw model to the top plate with the convex portion of the jaw model extending toward the base; a flask adapted to be seated on the base and to receive a mixture of plaster or other hardenable material; means for preventing the flask from moving on the base relative thereto.

BRIEF DESCRIPTION OF THE DRAWINGS

Further objects, features, and advantages of this invention will become apparent from the consideration of the following detailed description of a presently-preferred embodiment when taken in conjunction with the accompanying drawings, wherein.

DETAILED DESCRIPTION OF THE PREFERRED EMBODIMENT OF THE INVENTION

The present method and apparatus are usable in the fabrication of "adjustment-free" artificial dentures, and is especially adapted for use in making such "finished dentures" from their precise models, i.e., the "precise provisional dentures" therefor. Various dental procedures for forming such "precise provisional dentures" are known in the art, and it should be noted that this invention is not limited to any particular one of those procedures as its preparatory steps. However, in order to efficiently describe the preferred embodiment of this invention, it is instructive to first refer to a typical one of such dental procedures for making a "precise provisional denture".

The major steps involved in making a precise provisional denture are as follows:

1. An impression is taken by the dentist in suitable impression material that will harden in the mouth, to give negative impressions of the full upper and lower gum arches.

2. The negative gum impressions are then used to receive poured plaster material to form jaw models which are true reproductions of a patient's upper and lower gum arches.

3. A piece of synthetic resin compound or wax is attached on each jaw model and is so contoured to provide a provisional denture base for positioning artificial teeth thereon.

Figure 1A:
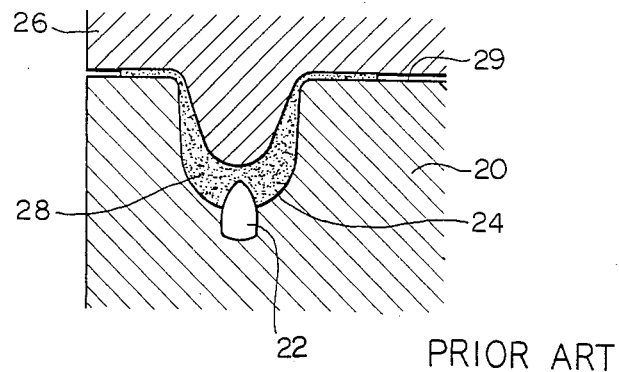
FIG. 1a is a fragmentary cross section of a synthetic resin denture sandwiched between the upper and lower plaster blocks, as constructed in accordance with the conventional dental procedure, showing how the curing synthetic resin compound penetrates into a narrow gap between the contiguous surfaces of the plaster blocks.
Figure 1B:
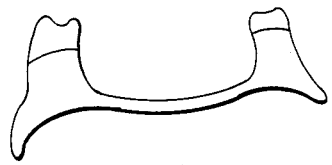
FIGS. 1b and 1c are schematic view, in cross section, showing examples of a provisional denture and a precise provisional denture, respectively.

4. The next step is to attach the artificial teeth to the provisional denture bases and remove the denture bases with the teeth from the jaw models to provide a set of "provisional dentures", as shown in FIG. 1b.

5. The dentist applies a predetermined quantity of tissue treatment material, such as shown at 27 in FIG. 1c, to the concave surfaces of the provisional denture bases and places them in the patient's mouth for the direct bite. The provisional denture bases are gradually adjusted, as may be necessary, until the relative size and shape hold the jaws in proper position corresponding to the normal closure position of the original teeth of the patient.

Figure 1C:
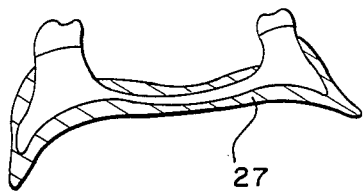

6. When this phase has been completed, the denture bases are removed from the patient's mouth. The denture bases thus adjusted in the patient's mouth and equipped with the artificial teeth, as shown in FIG. 1c will be hereinafter referred to as "precise provisional dentures".

7. The next step then becomes the initial step of the procedure or method of this invention, and will now be explained with reference to FIGS. 2 through 4 of the drawings.

Figure 2:
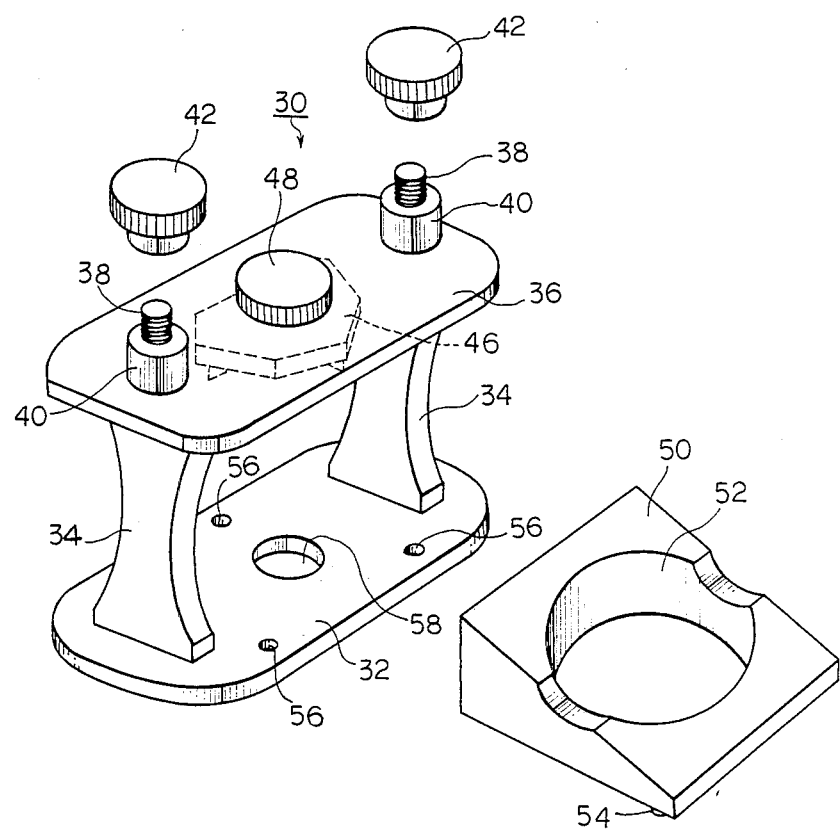
FIG. 2 is a perspective view of an improved jig used to fabricate artificial dentures in accordance with the teachings of this invention.

FIG. 2 is a perspective view of a jig constructed in accordance with this invention and especially adapted for use in making a set of "finished dentures" from the precise provisional dentures formed by following the preparatory steps just described. The jig 30 is formed with a base 32 from which a pair of posts 34 extend upwardly. Each post 34 includes a horizontally disposed planar top (not shown) for supporting a top plate 36 thereon, and a threaded guide stud 38 extending vertically upwardly from the top. Each guide stud 38 has a collar 40 and a locking screw 42 associated therewith. The top plate 36 includes an opening (not shown)

formed in the center thereof, for passing a threaded stud 44 on a holder plate 46 to which the patient's jaw model is adapted to be attached. The threaded stud 44 has a locking screw 48 associated therewith.

Also shown in FIG. 2 is a flask 50 which is generally square in cross section and formed with a circular opening 52. The flask 50 includes three pins 54 which are triangularly disposed and are adapted to be snugly received in complementary recesses 56 formed in the base 32 of the jig 30. The base 32 also includes an opening 58 in the center of the triangle defined by the three recesses 56, which opening is adapted to facilitate removal from the jig of a lower plaster block to be described later in more detail.

In order to make a set of finished dentures, the patient's precise jaw models 59 are first formed by pouring soft plaster into the concave portion of the precise provisional dentures and then allowing the plaster to harden. The precise jaw models 59 thus formed and equipped with the precise provisional dentures are then attached to the jig's holder plate 46 and, in turn, the holder plate 46 is mounted on the top plate 36 of the jig by fastening the locking screw 48.

Figure 3:
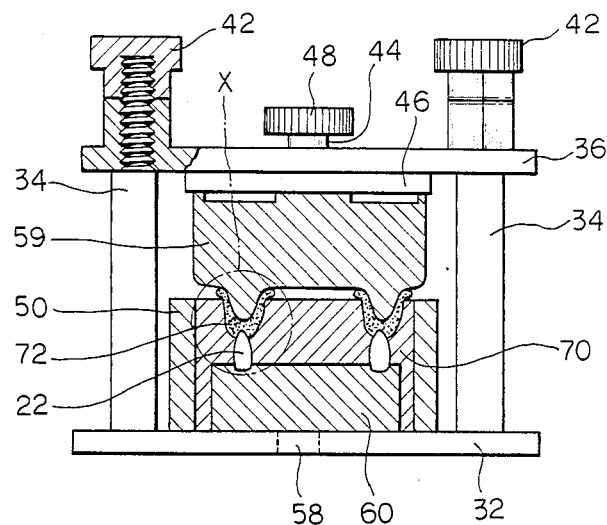
FIG. 3 is a front elevational view, partly in cross section, showing the jig in operative condition for fabricating an artificial denture.

Referring to FIG. 3, a piece of soft plaster is placed on the base 32 of the jig to provide a plaster pad 60 overlying the opening 58. While the soft plaster is still soft prior to complete solidification, the top plate 36 which is equipped with the holder plate 46 having attached thereto the precise jaw model 59 and the precise provisional denture is mounted on the jig by passing the guide studs 38 through the openings of the top plate 36 and their associated collars 40 and then fastening the associated locking screws 42. The mounting of the top plate 36 to the jig 30 will cause the tips of the artificial teeth 22 attached to the precise provisional denture supported by the precise jaw model 59 to penetrate into the soft plaster pad 60, so that when the top plate 36 is later removed from the jig upon solidification of the soft plaster, the imprints of the tips of the artificial teeth 22 are left on the plaster pad 60.

The individual teeth 22 on the precise provisional denture are then removed therefrom by heating the denture base to facilitate such a removal operation. Such removal of individual teeth is accomplished to ensure that only the artificial teeth will be left on a plaster block which is formed in a later step. The individual teeth thus removed are then restored to their original positions in the corresponding imprints on the plaster pad 60. Thereafter, the surface portions of each artificial tooth 22 which were covered by the provisional denture base are coated with fill-in molten wax in order to prevent the formation of a gap between the tooth and the provisional denture base which will be assembled together in a subsequent procedural step. An additional purpose of coating each tooth with the thin film of wax material is to prevent soft plaster from seeping into the gap when the soft plaster is poured into the flask to submerge the precise provisional denture equipped with the teeth.

Where the provisional denture bases are formed of wax rather than synthetic resin compound, the above-described steps of removing artificial teeth from the denture bases and then restoring them to their original positions can be dispersed with, thus resulting in a reduction in the time required to fabricate finished dentures. However, the denture bases formed of synthetic resin material offer advantages that they provide more natural bite than the wax denture bases because of the relative strength of the materials.

The top plate 36 equipped with the precise jaw model 59 and the precise provisional denture is then removed from the jig, and the flask 50 is firmly seated on the base 32 in a manner to surround the plaster pad 60. Thereafter, the top plate 36 with the holder plate 46, the precise jaw model 59 and the precise provisional denture supported thereby is again mounted in place on the jig 30 in such a manner that the tips of the artificial teeth are received in the respective imprints in the plaster pad 60.

A mixture of plaster material and water is then poured into the flask 50 to submerge the precise provisional denture therein. The plaster mixture will soon solidify to provide a plaster block 70 having a recess or concave surface 72 conforming to the actual shape of the precise provisional denture. To expose this concave surface 72 of the provisional denture, all the synthetic resin material and the tissue treating material, of which the denture base is comprised, are removed from the plaster block 70.

With the synthetic resin material removed, the plaster block 70 is now ready for the operation of filling a finish synthetic resin compound into the recess 72. Upon the completion of the filling operation, the top plate 36 is again mounted on the jig and the flask 50 is then heated to cure the finish synthetic resin compound due to polymerization.

Figure 4:
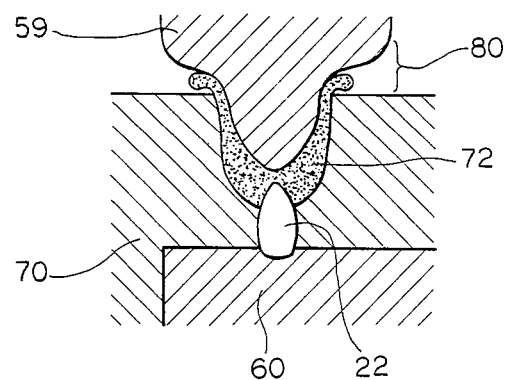
FIG. 4 is a detailed view of the encircled portion of FIG. 3, showing the manner in which the synthetic resin denture is formed in accordance with the teachings of this invention.

It will be apparent from FIG. 4, a detailed view of the encircled portion of FIG. 3, that during polymerization the finish synthetic resin compound is confined to a plenum defined by the concave surface 72 of the plaster block 70 and the convex surface of the precise jaw model 59. Any spillover of the synthetic resin compound during polymerization will escape into a wide clearance 80 between the precise jaw model 59 and the plaster block 70, without moving the jaw model upward away from the block which is different from the prior art arrangement of FIG. 1 wherein the curing synthetic resin compound penetrates into a narrow gap 29 inherently formed between the upper and lower plaster blocks resulting in an increase in the spacing therebetween.

It will be appreciated that in accordance with the teachings of this invention there has been provided a completely finished set of artificial dentures which fits the prescription satisfactorily and thus does not require frequent adjustments. To recapitulate the important features of this invention:

(1) This invention eliminates the prior art problems associated with a narrow gap between the contiguous surfaces of the upper and lower plaster blocks which form together a mold for the denture, by using the precise jaw model 59, in place of the upper plaster block 26, to provide a wide clearance 80 between the precise jaw model and the plaster block 70 so that any synthetic resin compound spilling over from the mold during polymerization will escape into the wide clearance thus bringing the shape of the molding cavity into precise conformity with the precise provisional denture without any upward movement of the jaw model away from the block.

(2) The use of the precise jaw model to provide such a wide clearance for allowing escape of a synthetic resin compound will eliminate the need for use of the expensive, heavy duty press conventionally required by the prior art procedures.

(3) The jig according to this invention is simple in construction and inexpensive to manufacture.

Numerous features and advantages of this invention have been set forth in the foregoing description, together with details of structure and function of the invention. The disclosure, however, is illustrative only, and changes may be made in detail without deviating from the true scope of the invention.

What is claimed is:

1. A method of fabricating a finished artificial denture, comprising:
   (1) making a precise provisional denture comprising a denture base and a plurality of artificial teeth thereon, the denture base having a concave surface conforming to the actual shape of an edentulous ridge in a patient's mouth by taking an impression of the endentulous ridge, forming a jaw model from the impression, attaching a synthetic resin compound or wax onto the jaw model to provide a provisional denture base for positioning artificial teeth thereon, attaching artificial teeth to the provisional denture base, removing the denture base with the attached teeth from the jaw model to provide a provisional denture, applying a predetermined quantity of tissue treatment material to the concave surface of the provisional denture base and adjusting the provisional denture base while it is in the patient's mouth thereby forming the precise provisional denture with an actual shape;
   (2) making a precise jaw model having a convex surface from the concave surface of the denture base of the precise provisional denture such that the precise jaw model provides for a wide clearance during subsequent molding of an artificial denture;
   (3) forming a block of plaster or other hardenable material having a recess therein that conforms to the actual shape of the precise provisional denture, the artificial teeth having their tips extending into the block and their roots extending into the recess having a concave surface;
   (4) filling a synthetic resin compound into the recess of the block;
   (5) forcing the precise jaw model to move into the recess of the block to mold the synthetic resin compound therein into the artificial denture;
   (6) subjecting the synthetic resin compound to a polymerization reaction to cause the compound to cure and solidly fill a plenum defined by the convex surface of the precise jaw model and the concave surface in the recess of the block; and
   (7) breaking the block apart upon solidification of the synthetic resin compound to provide a finished denture,
      wherein synthetic resin compound spilling over the plenum during polymerization escapes into the wide clearance formed between the precise jaw model and the block thereby avoiding any movement of the precise jaw model upwardly away from the block, and thereby resulting in the finished denture conforming to the actual shape of the precise provisional denture.

2. A method of fabricating a finished artificial denture, as defined in claim 1, in which the step (2) of making a precise jaw model comprises:
   (8) pouring a mixture of plaster or other hardenable material and solvent into the concave surface portion of the precise provisional denture and allowing the mixture to harden; and
   (9) attaching the hardened precise jaw model with the precise provisional denture to a holder plate.

3. A method of fabricating a finished artificial denture, as defined in claim 2, in which the mixture is soft plaster.

4. A method of fabricating a finished artificial denture, as defined in claim 3, in which the step (3) of forming a block comprises:
   (10) placing a piece of soft plaster on a base of a jig to provide a plaster pad;
   (11) mounting the holder plate having attached thereto the precise jaw model and the precise provisional denture to the jig while the soft plaster is still soft prior to solidification, in such a manner that the tips of the artificial teeth penetrate into the plaster pad;
   (12) removing the holder plate from the jig upon solidification of the soft plaster, leaving the imprints of the tips of the artificial teeth on the plaster pad;
   (13) seating a flask on the base of the jig in such a manner as to surround the plaster pad;
   (14) mounting the holder plate in place on the jig in such a manner that the tips of the artificial teeth are received in the respective imprints in the plaster pad;
   (15) pouring soft plaster into the flask to submerge the precise provisional denture therein;
   (16) allowing the soft plaster to solidify to provide a plaster block having the recess conforming to the actual shape of the precise provisional denture; and
   (17) removing from the plaster block all the material of which the precise provisional denture is comprised, upon solidification of the soft plaster, to expose the recess of the plaster block.

5. A method of fabricating a finished artificial denture, as defined in claim 4, in which the precise provisional denture is formed of a wax material.

6. A method of fabricating a finished artificial denture, as defined in claim 4, in which the precise provisional denture is formed of a synthetic resin material, further comprising:
   (18) removing the individual teeth on the precise provisional denture therefrom subsequently to the step (12);
   (19) restoring the individual teeth to their original positions in the corresponding imprints on the plaster pad; and
   (20) coating surface portions of each artificial tooth originally covered by the provisional denture base with fill-in molten wax to prevent formation of a gap between each tooth and the provisional denture base.

7. A method of fabricating a finished artificial denture, as defined in claim 4, in which the step (5) of forcing the precise jaw model to move into the recess comprises:
   (21) mounting the holder plate in place on the jig in such a manner that the synthetic resin compound is confined to the plenum defined by the concave surface in the recess of the plaster block and the convex surface of the precise jaw model, the plenum conforming exactly to the actual shape of the precise provisional denture.

8. A method of fabricating a finished artificial denture, as defined in claim 4, in which the step (6) of subjecting the synthetic resin compound to polymerization reaction comprises:
   (22) heating the flask so that the synthetic resin compound therein cures due to polymerization.

* * * * *